US007488475B2

(12) United States Patent
Young et al.

(10) Patent No.: US 7,488,475 B2
(45) Date of Patent: *Feb. 10, 2009

(54) ANTIBODY THERAPY OF TUMORS

(75) Inventors: David S. F. Young, Toronto (CA); Susan E. Hahn, Toronto (CA); Helen P. Findlay, Toronto (CA)

(73) Assignee: Arius Research, Inc., Toronto, Ontario (CA)

( * ) Notice: Subject to any disclaimer, the term of this patent is extended or adjusted under 35 U.S.C. 154(b) by 36 days.

This patent is subject to a terminal disclaimer.

(21) Appl. No.: 11/370,203

(22) Filed: Mar. 7, 2006

(65) Prior Publication Data

US 2006/0216234 A1  Sep. 28, 2006

Related U.S. Application Data

(60) Continuation-in-part of application No. 10/743,451, filed on Dec. 19, 2003, now abandoned, which is a continuation of application No. 10/348,231, filed on Jan. 21, 2003, now Pat. No. 7,009,040, and a continuation-in-part of application No. 10/891,866, filed on Jul. 15, 2004, now Pat. No. 7,186,808, which is a division of application No. 10/348,231.

(51) Int. Cl.
*A61K 39/395* (2006.01)
*C12P 21/04* (2006.01)
*C12P 21/08* (2006.01)
*C07K 16/00* (2006.01)

(52) U.S. Cl. .............. 424/133.1; 424/141.1; 424/155.1; 424/181.1; 424/183.1; 435/69.6; 530/387.3; 530/388.1; 530/388.8; 530/391.7

(58) Field of Classification Search ....................... None
See application file for complete search history.

(56) References Cited

U.S. PATENT DOCUMENTS

| | | | |
|---|---|---|---|
| 4,816,567 | A | 3/1989 | Cabilly et al. |
| 4,861,581 | A | 8/1989 | Epstein et al. |
| 5,171,665 | A | 12/1992 | Hellstrom et al. |
| 5,484,596 | A | 1/1996 | Hanna, Jr. et al. |
| 5,500,362 | A | 3/1996 | Robinson et al. |
| 5,693,763 | A | 12/1997 | Codington et al. |
| 5,750,102 | A | 5/1998 | Eisenbach et al. |
| 5,780,033 | A | 7/1998 | Torchillin et al. |
| 5,783,186 | A | 7/1998 | Arakawa et al. |
| 5,821,337 | A | 10/1998 | Carter et al. |
| 5,849,876 | A | 12/1998 | Linsley et al. |
| 5,869,045 | A | 2/1999 | Hellstrom et al. |
| 5,869,268 | A | 2/1999 | Kudo et al. |
| 6,180,357 | B1 | 1/2001 | Young et al. |
| 2004/0105816 | A1 | 6/2004 | Young et al. |
| 2005/0002940 | A1 | 1/2005 | Young et al. |

FOREIGN PATENT DOCUMENTS

| EP | 266032 | 5/1988 |
|---|---|---|
| EP | 404097 | 12/1990 |
| WO | WO9311161 | 6/1993 |
| WO | WO0034317 | 6/2000 |

OTHER PUBLICATIONS

Campbell et al. Biology, 5th ed. p. 856, 1999.*
L. Belanger et al, "Enzyme-linked immunoassay for alpha-fetoprotein by competitive and sandwich procedures", Clinica Chimica Acta., 48:15-18 (1973).
D. Blakey et al, "Antitumor activity of the novel vascular targeting agent ZD6126 in a panel of tumor models", Clinical Cancer Research, 8:1974-1983 (Jun. 2002).
N. Campbell et al, "Methods: Monoclonal antibody technology", Biology, 5th ed., pp. 856 (1999).
P. Capel et al, "Heterogeneity of human IgG Fc receptors", Immunomethods, 4:25-34 (1994).
M. Chatterjee et al, "Idiotypic antibody immunotherapy of cancer", Cancer Immunol. Immunother., 38:75-82 (1994).
C. Chothia et al, "Canonical structures for the hypervariable regions of immunoglobulins", J. Mol. Biol., 196:901-917 (1987).
T. Clackson et al, "Making antibody fragments using phage display libraries", Nature, 352:624-628 (Aug. 1991).
R. Clynes et al, "Fc receptors are required in passive and active immunity to melanoma", Proc. Natl. Acad. Sci. USA, 95:652-656 (Jan. 1998).
M. Co et al, "Humanized antibodies for therapy", Nature, 351(6):501-502 (Jun. 1991).
S. Eckhardt et al, "Developmental therapeutics: successes and failures of clinical trial designs of targeted compounds", ASCO Educational Book, 39th Annual Meeting, pp. 209-219 (2003).
B. Froehler et al, "Synthesis of DNA via deoxynucleoside H-phosphonate intermediates", Nucleic Acids Research, 14(13):5399-5407 (1986).
H. Gazzano-Santoro et al, "A non-radioactive complement-dependent cytotoxicity assay for anti-CD20 monoclonal antibody", J. Immunol. Methods, 202:163-171 (1997).
S. Guichard et al, "Schedule dependent activity of topotecan in OVCAR 3 ovarian carcinoma xenograft: pharmacokinetic and pharmacodynamic evaluation", Clinical Cancer Research, 7:3222-3228 (Oct. 2001).
N. Guilbard et al, "Marked antitumor activity of a new potent acronycine derivative in orthotopic models of human solid tumors", Clinical Cancer Research, 7:2573-2580 (Aug. 2001).
R. Guyer et al, "Immunoglobin binding by mouse intestinal epithelial cell receptors", J. Immunol., 117(2):587-593 (Aug. 1976).

(Continued)

*Primary Examiner*—David J. Blanchard
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

5 Claims, 6 Drawing Sheets

OTHER PUBLICATIONS

M. De Haas et al, "Review articles: FCγ receptors of phagocytes", J. Lab Clin. Med., 126:330-341 (1995).

S. Hirschfeld et al, "Oncology drug development: United States Food and Drug Administration Perspective", Critical Reviews in Oncology/Hematology, 42:137-143 (2002).

P. Holliger et al, "Diabodies: small bivalent and bispecific antibody fragments", Proc. Natl. Acad. Sci. USA, 90:6444-6448 (Jul. 1993).

R. Jain, "Barriers to drug delivery in solid tumors", Sci. Am., 271(1):58-65 (Jul. 1994).

E. Kabat et al, "Sequences of proteins of immunological interest", 5th ed. Public Health Service, National Institutes of Health, Bethesda, MD (1991).

T. Karpanen et al, "Vascular endothelial growth factor C promotes tumor lymphangiogenesis and intralymphatic tumor growth", Cancer Research, 61:1786-1790 (Mar. 2001).

G. Klement et al, "Differences in therapeutic indexes of combination metronomic chemotherapy and an anti-VEGFR 2 antibody in multidrug resistant human breast cancer xenografts", Clinical Cancer Research, 8:221-232 (Jan. 2002).

J. Kim et al, "Localization of the site of the murine IgG1 molecule that is involved in binding to the murine intestinal Fc receptor", Eur. J. Immunol., 24:2429-2434 (1994).

G. Kohler et al, "Continuous cultures of fused cells secreting antibody of predefined specificity", Nature, 256:495-497 (Aug. 1975).

J. Marks et al, "By-passing immunization human antibodies from V-gene libraries displayed on phage", J. Mol. Biol., 222:581-597 (1991).

M. Daeron, "Fc receptor biology", Annu. Rev. Immunol., 15:203-234 (1997).

S. Morrison et al, "Chimeric human antibody molecules: mouse antigen binding domains with human constant region domains", Proc. Natl. Acad. Sci. USA, 81:6851-6855 (Nov. 1984).

K. Olson et al, "Inhibition of prostate carcinoma establishment and metastatic growth in mice by an antiangiogenin monoclonal antibody", Int. J. Cancer, 98:923-929 (2002).

A. Pluckthun, "Antibodies from *Escherichia coli*", Handbook of Experimental Pharmacology, vol. 113, Chapter 11, pp. 269-315, Springer-Verlag, New York (1994).

L. Presta et al, "Engineering therapeutic antibodies for improved function", Biochemical Society Transactions, 30 (4):487-490 (2002).

J. Ravetch et al, "Fc receptors", Annu. Rev. Immunol., 9:457-492 (1991).

E. Rubinstein et al, "CD9, CD63, CD81, and CD82 are components of a surface tetraspan network connected to HLA-DR and VLA integrins", Eur. J. Immunol., 26:2657-2665 (1996).

S. Seaver, "Monoclonal antibodies in industry: more difficult than originally thought", Genetic Engineering News, 14 (14):10 and 21 (1994).

S. Shak, "Overview of the trastuzumab (Herceptin) anti-HER monoclonal antibody clinical program in HER2 overexpressing metastatic breast cancer", Seminars in Oncology, 26(4 Suppl 12):71-77 (Aug. 1999).

P. Smith et al, "Anti-interleukin 6 monoclonal antibody induces regression of human prostate cancer xenografts in nude mice", The Prostate, 48:47-53 (2001).

P. Therasse et al, "New guidelines to evaluate the response to treatment in solid tumors", J. Natl. Cancer Inst., 92 (3):205-216 (Feb. 2000).

V. Von Gruenigen et al, "Efficacy of intraperitoneal adenovirus mediated p53 gene therapy in ovarian cancer", Int. J. Gynecol. Cancer, 9:365-372 (1999).

W. Waud et al, "Characterization of in vivo mammary and prostate tumor xenograft models for growth and response to clinical anticancer agents", Contrib. Oncol. Basel. Karger, 54:305-315 (1999).

L. Weiner, "An overview of monoclonal antibody therapy of cancer", Seminars in Oncology, 26(4 Suppl 12):41-50 (Aug. 1999).

Z. Xiao et al, "Generation of a baculovirus recombinant prostate specific membrane antigen and its use in the development of a novel protein biochip quantitive immunoassay", Protein Expression and Purification, 19:12-21 (2000).

* cited by examiner

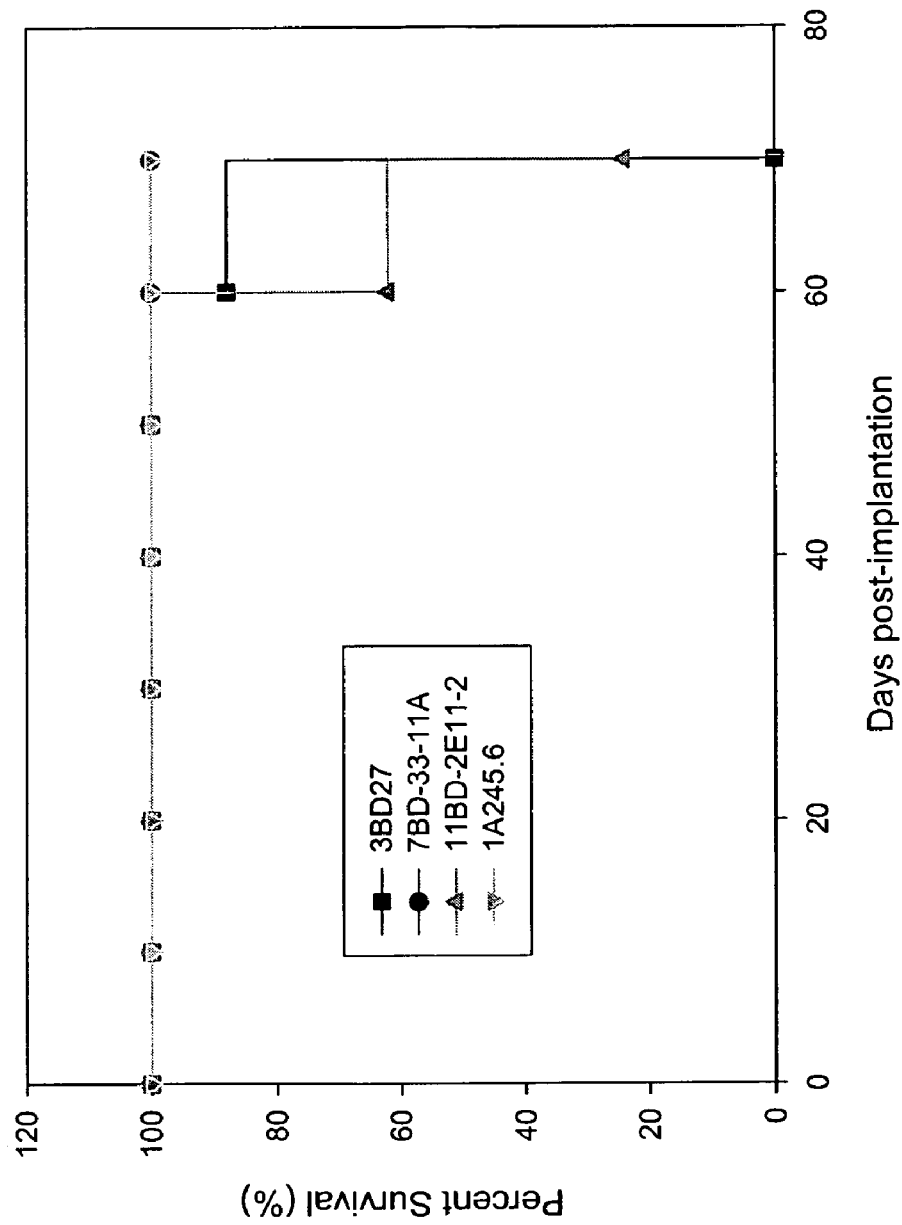

ANTIBODY THERAPY OF TUMORS

CROSS-REFERENCE TO RELATED APPLICATIONS

This application is a continuation-in-part of U.S. patent application Ser. No. 10/743,451, filed Dec. 19, 2003, now abandoned, which is a continuation of U.S. patent application Ser. No. 10/348,231, filed Jan. 21, 2003, now U.S. Pat. No. 7,009,040, issued Mar. 7, 2006, and is also a continuation-in-part of U.S. patent application Ser. No. 10/891,866, filed Jul. 15, 2004, now U.S. Pat. No. 7,186,808, issued Mar. 6, 2007, which is a divisional of U.S. patent application Ser. No. 10/348,231, filed Jan. 21, 2003, now U.S. Pat. No. 7,009,040, issued Mar. 7, 2006, the contents of which are herein incorporated by reference

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays which utilize the CDMABs of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30% of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment can not be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells.

Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-her 2 antibody in combination with Cisplatin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, had undergone Phase 2 clinical trials in over 60 patients with only one patient having a partial response. In other trials, use of 17-1A produced only one complete response and two minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung cancer, brain cancers, ovarian cancers, pancreatic cancer, prostate cancer, and stomach cancer. There has been some limited success in the use of anti-GD3 monoclonal antibody for melanoma. Thus, it can be seen that despite successful small animal studies that are a prerequisite for human clinical trials, the antibodies that have been tested have been for the most part ineffective.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

Furthermore, it is within the purview of this invention to conjugate standard chemotherapeutic modalities, e.g. radionuclides, with the CDMABs of the instant invention, thereby focusing the use of said chemotherapeutics.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C-1 component of the complement system thereby activating the classical pathway of complement activation which can lead to tumor lysis. For human antibodies the most effective complement activating antibodies are generally IgM and IgG 1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative cancer antigen that resides on the tumor cell. The second is the use of antibodies to target growth receptors and interfere with their function or to down regulate that receptor so that effectively its function is lost.

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies which are useful for in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

FIG. 6 is a graphical analysis quantifying percent survival over time relative to antibody therapy.

DETAILED DESCRIPTION OF THE INVENTION

Figure 1:
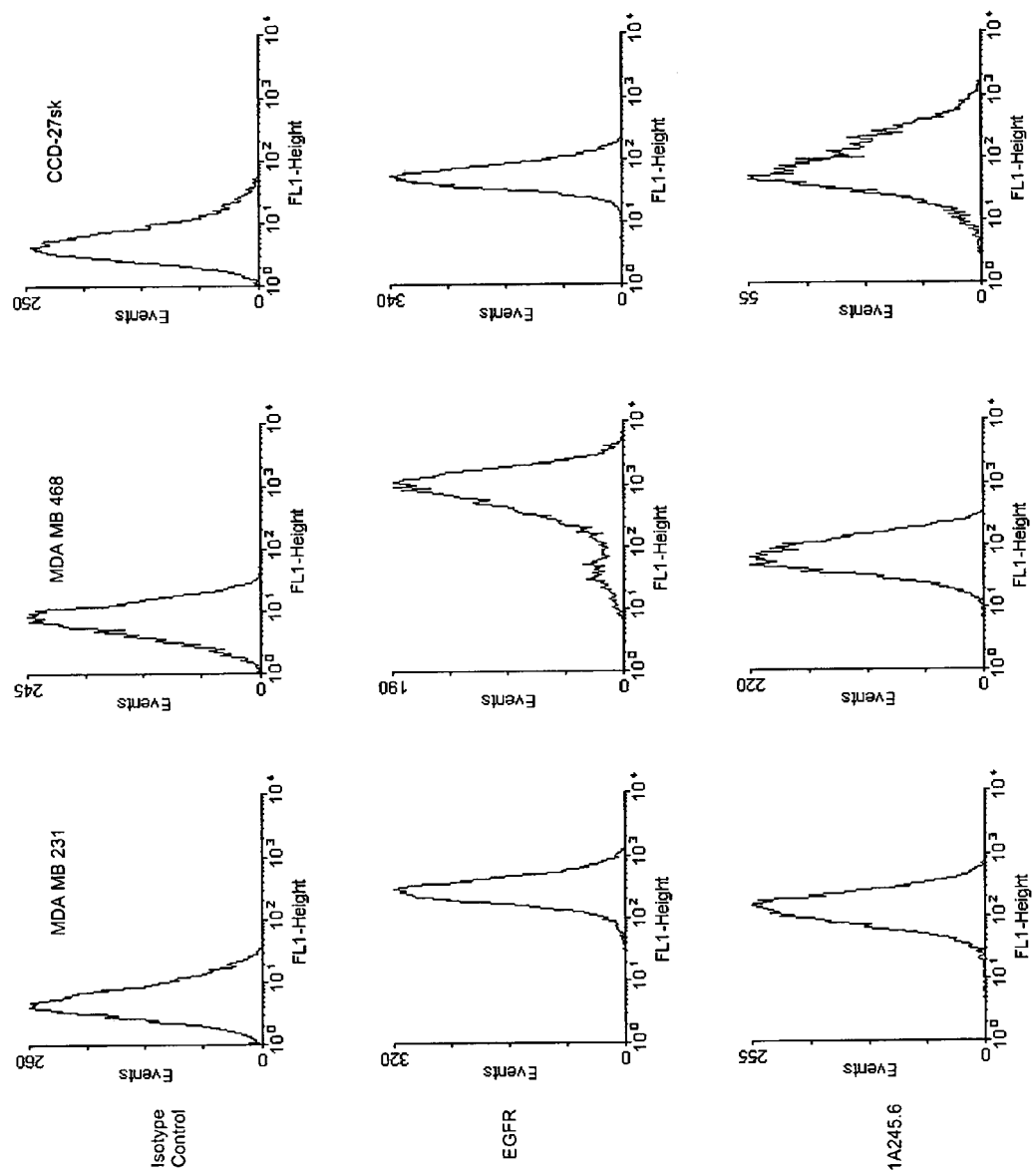
FIG. 1 includes representative FACS histograms of 1A245.6 antibodies, isotype control antibodies for both antibodies, anti-EGFR antibodies directed against several cancer cell lines and non-cancer cells.

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimerized or humanized antibodies), antibody compositions with polyepitopic specificity, single chain antibodies, immunoconjugates and fragments of antibodies (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Antibody fragments" comprise a portion of an intact antibody, preferably comprising the antigen-binding or variable region thereof. Examples of antibody fragments include less than full length antibodies, Fab, Fab', F(ab')$_2$, and Fv fragments; diabodies; linear antibodies; single-chain antibody molecules; single-chain antibodies, single domain antibody molecules, fusion proteins, recombinant proteins and multispecific antibodies formed from antibody fragment(s).

An "intact" antibody is one which comprises an antigen-binding variable region as well as a light chain constant domain (CL) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called a, d, e, ?, and μ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc?RIII only, whereas monocytes express Fc?RI, Fc?RII and Fc?RIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500, 362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Effector cells" are leukocytes which express one or more FcRs and perform effector functions. Preferably, the cells express at least Fc?RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the Fc?RI, Fc?RII, and Fc? RIII subclasses, including allelic variants and alternatively spliced forms of these receptors. Fc?RII receptors include Fc?RIIA (an "activating receptor") and Fc?RIIB (an "inhibiting receptor"), which have similar amino acid sequences that differ primarily in the cytoplasmic domains thereof. Activating receptor Fc?RIIA contains an immunoreceptor tyrosine-based activation motif (ITAM) in its cytoplasmic domain. Inhibiting receptor Fc?RIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, Annu. Rev. Immunol 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *Eur. J. Immunol.* 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the >sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (?) and lambda (?), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other protcinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful as a therapeutic or diagnostic agent in targeting a cell expressing the antigen. Where the antibody is one which binds a particular antigenic moiety it will usually preferentially bind that antigenic moiety as opposed to other receptors, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, camomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2?-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats, cows, etc. Preferably, the mammal herein is human.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.*, 14:5399-5407, 1986. They are then purified on polyacrylamide gels.

"Chimeric" antibodies are immunoglobulins in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al, *Proc. Natl. Acad. Sci. USA,* 81:6851-6855 (1984)).

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

"Homology" is defined as the percentage of residues in the amino acid sequence variant that are identical after aligning the sequences and introducing gaps, if necessary, to achieve the maximum percent homology. Methods and computer programs for the alignment are well known in the art.

Throughout the instant specification, hybridoma cell lines, as well as the isolated monoclonal antibodies which are produced therefrom, are alternatively referred to by their internal designation, 7BD-33-11A, 1A245.6, and 11BD-2E11-2 or Depository Designation PTA-4890, PTA-4889 and PTA-5643 respectively As used herein "ligand" includes a moiety which exhibits binding specificity for a target antigen, and which may be an intact antibody molecule and any molecule having at least an antigen-binding region or portion thereof (i.e., the variable portion of an antibody molecule), e.g., an Fv molecule, Fab molecule, Fab' molecule, F(ab').sub.2 molecule, a bispecific antibody, a fusion protein, or any genetically engineered molecule which specifically recognizes and binds the antigen bound by the isolated monoclonal antibody produced by the hybridoma cell line designated as, ATCC PTA-4890, ATCC PTA-4889, or ATCC PTA-5643, (the ATCC PTA-4890, ATCC PTA-4889, or ATCC PTA-5643 antigen).

As used herein "antigen-binding region" means a portion of the molecule which recognizes the target antigen.

As used herein "competitively inhibits" means being able to recognize and bind a determinant site to which the monoclonal antibody produced by the hybridoma cell line designated as ATCC PTA-4890, ATCC PTA-4889, or ATCC PTA-5643, (ATCC PTA-4890, ATCC PTA-4889, or ATCC PTA-5643 antibody) is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the ATCC PTA-4890, ATCC PTA-4889, or ATCC PTA-5643, antigen or portions thereof.

As used herein, an "immunoconjugate" means any molecule or ligand such as an antibody chemically or biologically linked to a cytotoxin, a radioactive agent, enzyme, toxin, an anti-tumor drug or a therapeutic agent. The antibody may be linked to the cytotoxin, radioactive agent, anti-tumor drug or therapeutic agent at any location along the molecule so long as it is able to bind its target. Examples of immunoconjugates include antibody toxin chemical conjugates and antibody-toxin fusion proteins.

As used herein, a "fusion protein" means any chimeric protein wherein an antigen binding region is connected to a biologically active molecule, e.g., toxin, enzyme, or protein drug.

In order that the invention herein described may be more fully understood, the following description is set forth.

The present invention provides ligands (i.e., ATCC PTA-4890, ATCC PTA-4889, or ATCC PTA-5643 ligands) which specifically recognize and bind the ATCC PTA-4890, ATCC PTA-4889, or ATCC PTA-5643 antigen.

The ligand of the invention may be in any form as long as it has an antigen-binding region which competitively inhibits the immunospecific binding of the monoclonal antibody produced by hybridoma ATCC PTA-4890, ATCC PTA-4889, or ATCC PTA-5643, to its target antigen. Thus, any recombinant proteins (e.g., fusion proteins wherein the antibody is combined with a second protein such as a lymphokine or a tumor inhibitory growth factor) having the same binding specificity as the ATCC PTA-4890, ATCC PTA-4889, or ATCC PTA-5643, antibody fall within the scope of this invention.

In one embodiment of the invention, the ligand is the ATCC PTA-4890, ATCC PTA-4889, or ATCC PTA-5643 antibody.

In other embodiments, the ligand is an antigen binding fragment which may be a Fv molecule (such as a single chain Fv molecule), a Fab molecule, a Fab' molecule, a F(ab')2 molecule, a fusion protein, a bispecific antibody, a heteroantibody or any recombinant molecule having the antigen-binding region of the ATCC PTA-4890, ATCC PTA-4889, or ATCC PTA-5643 antibody. The ligand of the invention is directed to the epitope to which the ATCC PTA-4890, ATCC PTA-4889, or ATCC PTA-5643 monoclonal antibody is directed.

The ligand of the invention may be modified, i.e., by amino acid modifications within the molecule, so as to produce derivative molecules. Chemical modification may also be possible.

Derivative molecules would retain the functional property of the polypeptide, namely, the molecule having such substitutions will still permit the binding of the polypeptide to the ATCC PTA-4890, ATCC PTA-4889, or ATCC PTA-5643 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Given an antibody, an individual ordinarily skilled in the art can generate a competitively inhibiting ligand, for example a competing antibody, which is one that recognizes the same epitope (Belanger et al., 1973). One method could entail immunizing with an immunogen that expresses the antigen recognized by the antibody. The sample may include but is not limited to tissue, isolated protein(s) or cell line(s). Resulting hybridomas could be screened using a competing assay, which is one that identifies antibodies that inhibit the binding of the test antibody, such as ELISA, FACS or immunoprecipiation. Another method could make use of phage display libraries and panning for antibodies that recognize said antigen (Rubinstein et al., 2003). In either case, hybridomas would be selected based on their ability to out-compete the binding of the original antibody to its target antigen. Such hybridomas would therefore possess the characteristic of recognizing the same antigen as the original antibody and more specifically would recognize the same epitope.

EXAMPLE 1

Hybridomas Production—Hybridoma Cell Line 7BD-33-11A, 1A245.6, 11BD-2E11-2

Hybridomas:

The hybridoma cell lines 7BD-33-11A and 1A245.6 were deposited, in accordance with the Budapest Treaty, with the American Type Culture Collection, 10801 University Blvd., Manassas, Va. 20110-2209 on Jan. 8, 2003, under Accession Number PTA-4890 and PTA-4889, respectively. In accordance with 37 CFR 1.808, the depositors assure that all restrictions imposed on the availability to the public of the deposited materials will be irrevocably removed upon the granting of a patent.

The hybridoma cell line 11BD-2E11-2 was deposited, in accordance with the Budapest Treaty, with the American Type Culture Collection, 10801 University Blvd., Manassas, Va. 20110-2209 on Nov. 11, 2003, under Accession Number PTA-5643. In accordance with 37 CFR 1.808, the depositors assure that all restrictions imposed on the availability to the public of the deposited materials will be irrevocably removed upon the granting of a patent.

To produce the hybridoma that produce the anti-cancer antibody 7BD-33-11A single cell suspensions of the antigen, i.e. human breast cancer cells, were prepared in cold PBS. Eight to nine weeks old BALB/c mice were immunized by injecting 100 microliters of the antigen-adjuvant containing between 0.2 million and 2.5 million cells in divided doses both subcutaneously and intraperitoneally with Freund's Complete Adjuvant. Freshly prepared antigen-adjuvant was used to boost the immunized mice at between 0.2 million and 2.5 million cells in the same fashion three weeks after the initial immunization, and two weeks after the last boost. A spleen was used for fusion at least two days after the last immunization. The hybridomas were prepared by fusing the isolated splenocytes with Sp2/0 myeloma partners. The supernatants from the fusions were tested for subcloning of the hybridomas.

To produce the hybridoma that produce the anti-cancer antibody 1A245.6 single cell suspensions of the antigen, i.e. human breast cancer cells, were prepared in cold PBS. Eight to nine weeks old BALB/c mice were immunized by injecting 100 microliters of the antigen-adjuvant containing 2.5 million cells in divided doses both subcutaneously and intraperitoneally with Freund's Complete Adjuvant. Freshly prepared antigen-adjuvant was used to boost the immunized mice at 2.5 million cells in the same fashion three weeks after the initial immunization, two weeks later, five weeks later and three weeks after the last boost. A spleen was used for fusion at least three days after the last immunization. The hybridomas were prepared by fusing the isolated splenocytes with NSO-1 myeloma partners. The supernatants from the fusions were tested for subcloning of the hybridomas.

To produce the hybridoma that produce the anti-cancer antibody 11BD-2E11-2 single cell suspensions of the antigen, i.e. human breast cancer cells, were prepared in cold PBS. Eight to nine weeks old BALB/c mice were immunized by injecting 100 microliters of the antigen-adjuvant containing between 0.2 million and 2.5 million cells in divided doses both subcutaneously and intraperitoneally with Freund's Complete Adjuvant. Freshly prepared antigen-adjuvant was used to boost the immunized mice at between 0.2 million and 2.5 million cells in the same fashion two to three weeks after the initial immunization, and two weeks after the last boost. A spleen was used for fusion at least two days after the last immunization. The hybridomas were prepared by fusing the isolated splenocytes with NSO-1 myeloma partners. The supernatants from the fusions were tested for subcloning of the hybridomas.

To determine whether the antibodies secreted by hybridoma cells are of the IgG or IgM isotype, an ELISA assay was employed. 100 microliters/well of goat anti-mouse IgG+IgM (H+L) at a concentration of 2.4 micrograms/mL in coating buffer (0.1M carbonate/bicarbonate buffer, pH 9.2-9.6) at 4° C. was added to the ELISA plates overnight. The plates were washed thrice in washing buffer (PBS+0.05% Tween). 100 microliters/well blocking buffer (5% milk in wash buffer) was added to the plate for 1 hr. at room temperature and then washed thrice in washing buffer. 100 microliters/well of hybridoma supernatant was added and the plate incubated for 1 hr. at room temperature. The plates were washed thrice with washing buffer and 1/5000 dilution of either goat anti-mouse IgG or IgM horseradish peroxidase conjugate (diluted in PBS containing 1% bovine serum albumin), 100 microliters/well, was added. After incubating the plate for 1 hr. at room temperature the plate was washed thrice with washing buffer. 100 microliters/well of TMB solution was incubated for 1-3 minutes at room temperature. The color reaction was terminated by adding 100 microliters/well 2M $H_2SO_4$ and the plate was read at 450 nm with a Perkin-Elmer HTS7000 plate reader. As indicated in Table 1 the 7BD-33-11A, 1A245.6, 11BD-2E11-2 hybridomas secreted primarily antibodies of the IgG isotype.

After one to four rounds of limiting dilution hybridoma supernatants were tested for antibodies that bound to target cells in a cell ELISA assay. Three breast cancer cell lines were tested: MDA-MB-231 (also referred to as MB-231), MDA-MB-468 (also referred to as MB-468), and SKBR-3. The plated cells were fixed prior to use. The plates were washed thrice with PBS containing $MgCl_2$ and $CaCl_2$ at room temperature. 100 microliters of 2% paraformaldehyde diluted in PBS was added to each well for ten minutes at room temperature and then discarded. The plates were again washed with PBS containing $MgCl_2$ and $CaCl_2$ three times at room temperature. Blocking was done with 100 microliters/well of 5% milk in wash buffer (PBS+0.05% Tween) for 1 hr at room temperature. The plates were washed thrice with wash buffer and the hybridoma supernatant was added at 100 microliters/well for 1 hr at room temperature. The plates were washed three times with wash buffer and 100 microliters/well of 1/5000 dilution of goat anti-mouse IgG or IgM antibody conjugated to horseradish peroxidase (diluted in PBS containing 1% bovine serum albumin) was added. After a one hour incubation at room temperature the plates were washed three times with wash buffer and 100 microliter/well of TMB substrate was incubated for 1-3 minutes at room temperature. The reaction was terminated with 100 microliters/well 2M $H_2SO_4$ and the plate read at 450 nm with a Perkin-Elmer HTS7000 plate reader. The results as tabulated in Table 1 were expressed as the number of folds above background compared to the IgG isotype control (3BD-27). The antibodies from the 7BD-33-11A and 1A245.6 hybridoma cell lines bound strongly to all 3 breast lines, with binding at least 6 times greater than background. Both antibodies bound most strongly to the MDA-MB-231 cell line. The antibodies from the 11BD-2E11-2 hybridoma cell line also bound most strongly to the MDA-MB-231 cell line, but did not demonstrate binding on the other 2 cell lines greater than background. These results suggest that the epitope recognized by this antibody is not present on MDA-MB-468 or SKBR-3 cells, and is distinct from the epitopes recognized by 7BD-33-11A and 1A245.6.

In conjunction with testing for antibody binding the cytotoxic effect of the hybridoma supernatants were tested in the same breast cancer cell lines: MDA-MB-231, MDA-MB-468 and SKBR-3. The Live/Dead cytotoxicity assay was obtained from Molecular Probes (Eu,OR). The assays were performed according to the manufacturer's instructions with the changes outlined below. Cells were plated before the assay at the predetermined appropriate density. After 2 days, 100 microliters of supernatant from the hybridoma microtitre plates were transferred to the cell plates and incubated in a 5% $CO_2$ incubator for 5 days. The wells that served as the positive controls were aspirated until empty and 100 microliters of sodium azide and/or cycloheximide was added. 3BD-27 monoclonal antibody was also added as an isotype control since it was known not to bind to the three breast cancer cell lines being tested. An anti-EGFR antibody (C225) was also used in the assay for comparison. After 5 days of treatment, the plate was then emptied by inverting and blotted dry. Room temperature DPBS containing $MgCl_2$ and $CaCl_2$ was dispensed into each well from a multichannel squeeze bottle, tapped three times, emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel. The results were tabulated in Table 1.

Differential cytotoxicity was observed with the 3 antibodies. 11BD-2E11-2 demonstrated killing of 39-73%, with the highest cytotoxicity observed in SKBR-3 cells. 1A245.6 and 7BD-33-11A demonstrated similar cytotoxicity in MDA-MB-231 cells, but 1A245.6 was also cytotoxic to MDA-MB-468 cells, while 7BD-33-11A was not.

This indicated the antibody derived form the hybridoma cell can produce cytotoxicity in cancer cells. There was also a general association between the degree of antibody binding and the cytotoxicity produced by the hybridoma supernatants. There were several exceptions to this trend such as the amount of cytotoxicity produced by 11BD-2E11-2 in MB-468 cancer cells, and SKBR-3 cancers despite a paucity of binding. This suggested that the antibody has a mediating action that was not detected by the cell ELISA binding assay in this cell type, or the assay did not detect the binding, which may be due to the constraints of the assay such as cell fixation. Finally, there existed yet another possibility, that is, the assay was not sensitive enough to detect the binding that was sufficient to mediate cytotoxicity in this particular situation. The other exception was the relative paucity of cytotoxicity of 7BD-33-11A towards MB-468 cells despite a 6 fold increase in binding over the background in comparison to an isotype control. This pointed to the possibility that binding was not necessarily predictive of the outcome of antibody ligation of its cognate antigen. The known non-specific cytotoxic agents cycloheximide produced cytotoxicity as expected.

TABLE 1

|  | Cytotoxicity (%) | | | | | | Binding (above bkgd) | | |
|---|---|---|---|---|---|---|---|---|---|
|  | MB-231 | | MB-468 | | SKBR-3 | | MB-231 | MB-468 | SKBR-3 |
| Clone | Average | CV | Average | CV | Average | CV | Fold | Fold | Fold |
| 1A245.6 | 17 | 7 | 13 | 5 | 44 | 8 | 23 | 10 | 16 |
| 7BD-33-11A | 16 | 2 | 2 | 2 | 29 | 3 | 13 | 6 | 9 |
| 11BD-2E11-2 | 39 | 2 | 66 | 1 | 73 | 18 | 11 | 2 | 1 |
| Cycloheximide | 49 | 9 | 24 | 5 | 56 | 14 |  |  |  |

EXAMPLE 2

Antibody Production

Monoclonal antibodies were produced by culturing the hybridomas, 7BD-33-11A, 11A245.6, 11BD-2E 11-2, in CL-1000 flasks (BD Biosciences, Oakville, ON) with collections and reseeding occurring twice/week and standard antibody purification procedures with Protein G Sepharose 4 Fast Flow (Amersham Biosciences, Baie d'Urfé, QC). It is within the scope of this invention to utilize monoclonal antibodies which are humanized, chimerized or murine antibodies. 7BD-33-11A, 1A245.6, 11BD-2E 11-2 were compared to a number of both positive (anti-Fas (EOS9.1, IgM, kappa, 20 micrograms/mL, eBioscience, San Diego, Calif.), anti-Her2/neu (IgG1, kappa, 10 microgram/mL, Inter Medico, Markham, ON), anti-EGFR(C225, IgG1, kappa, 5 microgram/mL, Cedarlane, Romby, ON), Cycloheximide (100 micromolar, Sigma, Oakville, ON), $NaN_3$ (0.1%, Sigma, Oakville, ON)) and negative (107.3 (anti-TNP, IgG1, kappa, 20 microgram/mL, BD Biosciences, Oakville, ON), G155-178 (anti-TNP, IgG2a, kappa, 20 micro gram/mL, BD Biosciences, Oakville, ON), MPC-11 (antigenic specificity unknown, IgG2b, kappa, 20 microgram/mL), J606 (anti-fructosan, IgG3, kappa, 20 microgram/mL), IgG Buffer (2%)) controls in a cytotoxicity assay (Table 2). Breast cancer (MB-231, MB-468, MCF-7), colon cancer (HT-29, SW1116, SW620), lung cancer (NCI H460), ovarian cancer (OVCAR), prostate cancer (PC-3), and non-cancer (CCD 27sk, Hs888 Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, 100 microliters of purified antibody was diluted into media, and then were transferred to the cell plates and incubated in a 8% $CO_2$ incubator for 5 days. The plate was then emptied by inverting and blotted dry. Room temperature DPBS containing $MgCl_2$ and $CaCl_2$ was dispensed into each well from a multichannel squeeze bottle, tapped three times, emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel and the results were tabulated in Table 2. The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 2 represented inconsistent or effects less than the threshold cytotoxicity. The 7BD-33-11A and 1A245.6 antibodies demonstrated cytotoxicity in breast and prostate tumor cell lines selectively, while having no effect on non-transformed normal cells. Both demonstrated a 25-50% greater killing than the positive control anti-Fas antibody. 11BD-2E11-2 was specifically cytotoxic in breast and ovarian cancer cells, and did not affect normal cells. The chemical cytotoxic agents induced their expected cytotoxicity while a number of other antibodies which were included for comparison also performed as expected given the limitations of biological cell assays. In toto, it was shown that the three antibodies have cytotoxic activity against a number of cancer cell types. The antibodies were selective in their activity since not all cancer cell types were susceptible. Furthermore, the antibodies demonstrated functional specificity since they did not produce cytotoxicity against non-cancer cell types, which is an important factor in a therapeutic situation.

TABLE 2

|  |  | BREAST | | | COLON | | | LUNG | OVARY | PROSTATE | NORMAL | |
|---|---|---|---|---|---|---|---|---|---|---|---|---|
|  |  | MB-231 | MB-468 | MCF-7 | HT-29 | SW1116 | SW620 | NCI H460 | OVCAR | PC-3 | CCD 27sk | Hs888 Lu |
|  | 11BD2E11-2 | − | − | + | − | − | − | − | + | − | − | − |
|  | 7BD-33-11A | − | − | + | − | − | − | − | − | ++ | − | − |
|  | 1A245.6 | − | − | + | − | − | − | − | − | ++ | − | − |
| Positive Controls | anti-Fas | − | − | +++ | − | − | − | +++ | + | − | − | + |
|  | anti-Her2 | + | − | + | − | − | − | − | + | − | − | − |
|  | anti-EGFR | − | +++ | + | − | +++ | − | − | + | − | + | − |
|  | CHX (100 μM) | +++ | +++ | +++ | +++ | +++ | +++ | +++ | +++ | +++ | +++ | +++ |
|  | $NaN_3$ (0.1%) | +++ | +++ | +++ | +++ | − | − | +++ | +++ | +++ | − | − |
| Negative Controls | IgG1 |  |  |  |  |  |  |  | +++ |  | + |  |
|  | IgG2a |  |  | +++ |  | + |  |  |  |  |  |  |
|  | IgG2b |  |  | +++ |  |  |  |  |  |  |  |  |
|  | IgG3 |  |  |  |  |  |  |  |  |  |  |  |
|  | IgG Buffer |  | + |  |  |  |  |  |  |  |  |  |

Cells were prepared for FACS by initially washing the cell monolayer with DPBS (without $Ca^{++}$ and $Mg^{++}$). Cell dissociation buffer (INVITROGEN) was then used to dislodge the cells from their cell culture plates at 37° C. After centrifugation and collection the cells were resuspended in Dulbecco's phosphate buffered saline containing $MgCl_2$, $CaCl_2$ and 25% fetal bovine serum at 4° C. (wash media) and counted, aliquoted to appropriate cell density, spun down to pellet the cells and resuspended in staining media (DPBS containing $MgCl_2$ and $CaCl_2$) containing 7BD-33-11A, 1A245.6, 11BD-2E11-2 or control antibodies (isotype control or anti-EGF-R) at 20 micrograms/mL on ice for 30 minutes. Prior to the addition of Alexa Fluor 488-conjugated secondary antibody the cells were washed once with wash media. The Alexa Fluor 488-conjugated antibody in staining media was then added for 20 minutes. The cells were then washed for the final time and resuspended in staining media containing 1 microgram/mL propidium iodide. Flow cytometric acquisition of the cells was assessed by running samples on a FACScan using the CellQuest software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescence intensity of approximately 1-5 units. Live cells were acquired by gating for FSC and propidium iodide exclusion. For each sample, approximately 10,000 live cells were acquired for analysis and the resulted presented in Table 3. Table 3 tabulated the mean fluorescence intensity fold increase above isotype control and is presented qualitatively as: less than 5 (−); 5 to 50 (+); 50 to 100 (++); above 100 (+++) and in parenthesis, the percentage of cells stained.

EXAMPLE 3

Figure 5:
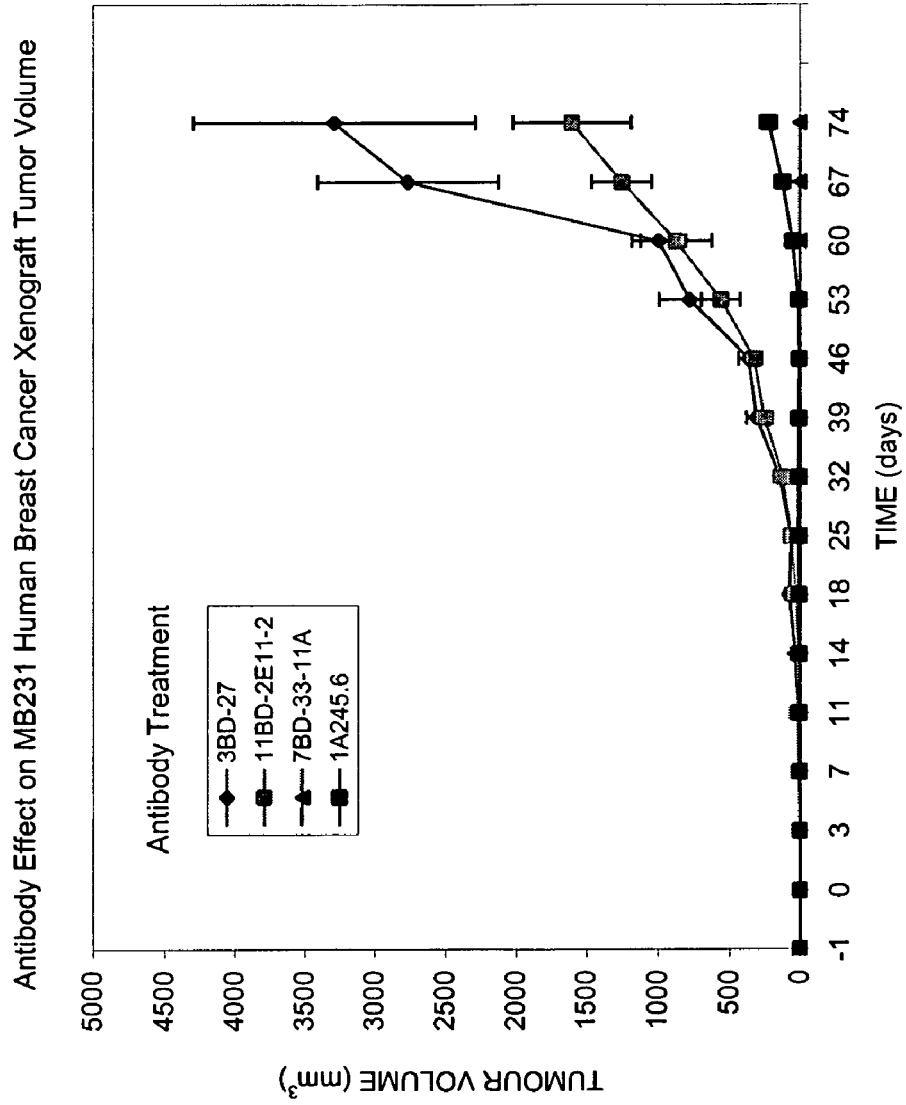
FIG. 5 is a graphical analysis of antibody effect on MB231 Human Breast Cancer tumor volume over time.

In Vivo Experiments:

Now with reference to the data shown in FIGS. 5 and 6, four to eight week old, female SCID mice were implanted with 5 million MDA-MB-231 human breast cancer cells in one hundred microliters injected subcutaneously in the scruff of the neck. The mice were randomly divided into four treatment groups of ten. On the day prior to implantation 20 mg/kg of either 11BD2E-11-2, 7BD-33-11A, 1A245.6 test antibodies or 3BD-27 isotype control antibody (known not to bind MDA-MB-231 cells) were administered intrapertioneally at a volume of 300 microliters after dilution from the stock concentration with a diluent that contained 2.7 mM KCl, 1 mM $KH_2PO_4$, 137 mM NaCl, 20 mM $Na_2HPO_4$. The antibodies were then administered once per week for a period of 7 weeks in the same fashion.

Tumor growth was measured about every seventh day with calipers for up to ten weeks or until individual animals reached the Canadian Council for Animal Care (CCAC) endpoints. Body weights of the animals were recorded for the duration of the study. At the end of the study all animals were euthanised according to CCAC guidelines. There were no clinical signs of toxicity throughout the study. Body weight measured at weekly intervals was a surrogate for well-being and failure to thrive. There was a minimal difference in weight for the groups treated with the isotype control, 3BD-27, and 7BD-33-11A, 1A245.6, or 11BD-2E11-2. At day 60 (11 days after the cessation of treatment) tumor volume of the group treated with 1A245.6 was 5.2% of the control group (p=0.0002) and demonstrated effectiveness at reducing tumor

TABLE 3

| Antibody | Isotype | BREAST | | | COLON | | | LUNG | OVARY | PROSTATE |
| | | MB-231 | MB-468 | MCF-7 | HT-29 | SW1116 | SW620 | NCI H460 | OVCAR | PC-3 |
| --- | --- | --- | --- | --- | --- | --- | --- | --- | --- | --- |
| 11BD2E11-2 | IgG1, k | +(61%) | − | − | − | − | − | − | − | − |
| 7BD-33-11A | IgG2a, k | +(96%) | − | +(76%) | +(97%) | +(34%) | +(bimodal, 76%) | +(bimodal, 60%) | +(51%) | +(75%) |
| 1A245.6 | IgG1, k | +(98%) | +(78%) | +(74%) | ++ | +(23%) | +(bimodal, 71%) | +(bimodal, 70%) | +(73%) | +(bimodal, 72%) |
| anti-EGFR | IgG1, k | ++ | ++bimodal | − | +(97%) | +(43%) | − | +(bimodal, 80%) | +(90%) | +(96%) |
| anti-FAS | IgM, k | − | − | − | +(30%) | − | − | +(61%) | − | − |

Figure 2:
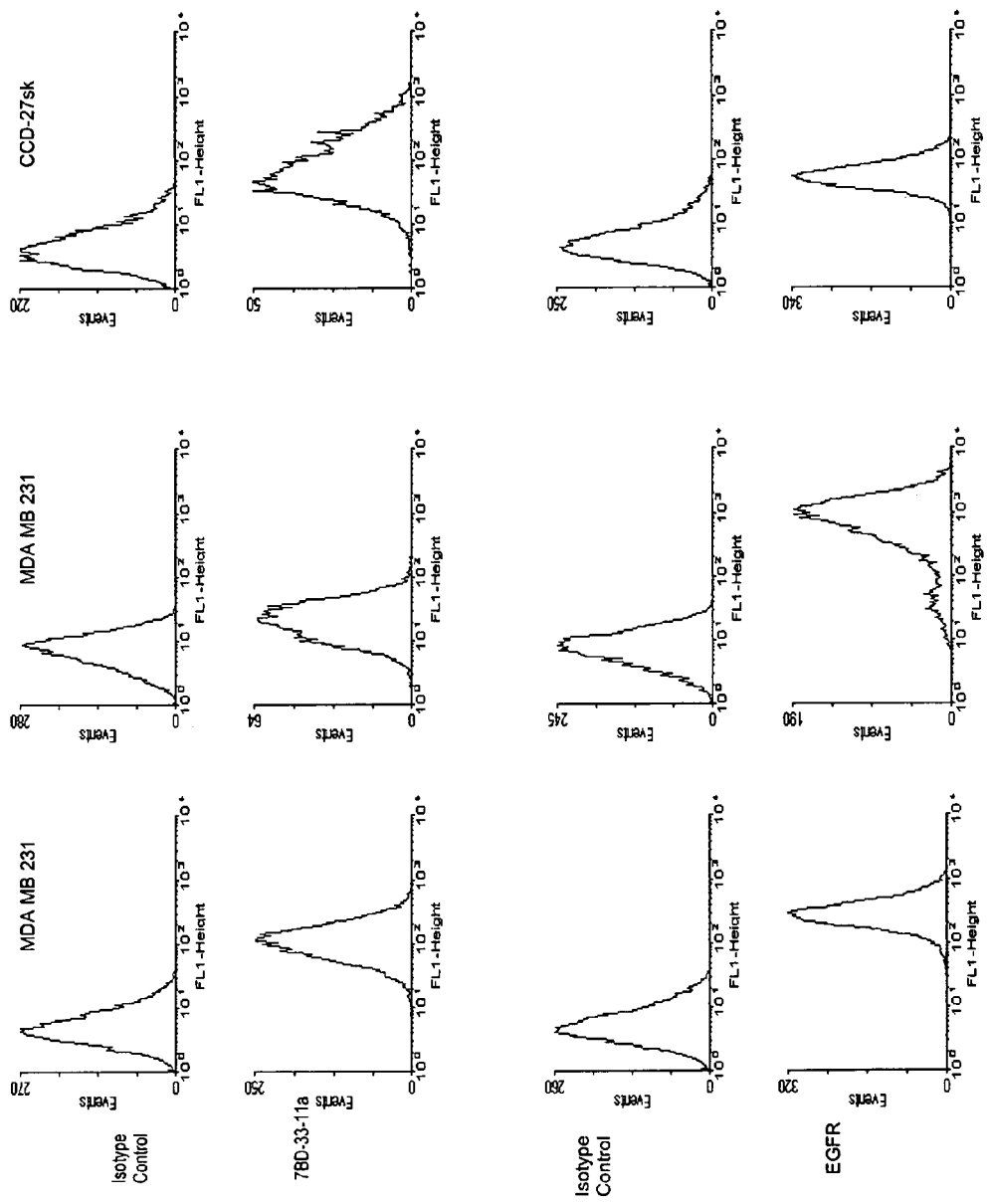
FIG. 2 includes representative FACS histograms of 7BD-33-11A antibodies, isotype control antibodies for 1A245.6, anti-EGFR antibodies, isotype control antibodies for anti-EGFR directed against several cancer cell lines and non-cancer cells.
Figure 3:
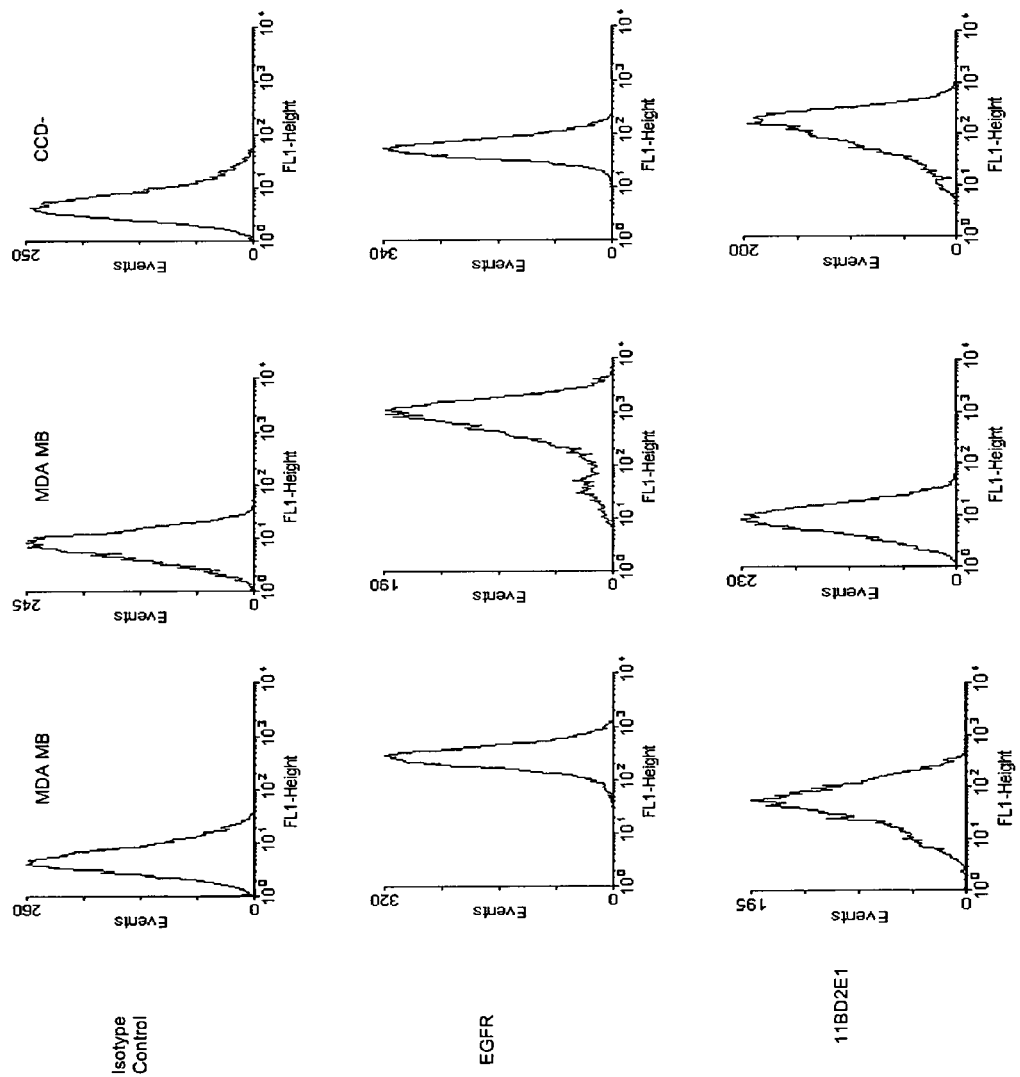
FIG. 3 includes representative FACS histograms of 11BD-2E11-2 antibodies, isotype control antibodies for both antibodies, anti-EGFR antibodies directed against several cancer cell lines and non-cancer cells.

Representative histograms of 7BD-33-11A antibodies were compiled for FIG. 1, 1A245.6 antibodies were compiled for FIG. 2, 11BD-2E11-2 were compiled for FIG. 3 and evidence the binding characteristics, inclusive of illustrated bimodal peaks, in some cases. 11BD-2E11-2 displayed specific tumor binding to the breast tumor cell line MDA-MB-231. Both 7BD-33-11A and 11A245.6 displayed similar binding to cancer lines of breast (MDA-MB-231 and MCF-7), colon, lung, ovary, and prostate origin and differential binding to one of the breast cancer cell lines (MDA-MB-468). There was binding of all three antibodies to non-cancer cells, however that binding did not produce cytotoxicity. This was further evidence that binding was not necessarily predictive of the outcome of antibody ligation of its cognate antigen, and was a non-obvious finding. This suggested that the context of antibody ligation in different cells was determinative of cytoxicity rather than just antibody binding.

burden with antibody treatment. Those mice bearing cancer treated with 7BD-33-11A antibody were disease free and had no tumor burden. The tumor volume was lower in the 11BD-2E 11-2 treatment group (45% of control) at day 67 (p=0.08). This also demonstrated a lesser tumor burden with cytotoxic antibody treatment in comparison to a control antibody. There was also corresponding survival benefits (FIG. 6) from treatment with 7BD-33-11A, 1A245.6, and 11BD-2E11-2 cytotoxic antibodies. The control group treated with 3BD-27 antibody reached 100% mortality by day 74 post-implantation. In contrast, groups treated with 7BD-33-11A were disease free and 1A245.6 treated animal displayed 100% survival and the group treated with 11BD-2E11-2 had 24% survival.

In toto, cytotoxic antibody treatment produced a decreased tumor burden and increased survival in comparison to a control antibody in a well recognized model of human cancer disease suggesting pharmacologic and pharmaceutical benefits of these antibodies (7BD-33-11A, 1A245.6, 11BD-2E11-2) for therapy in other mammals, including man.

EXAMPLE 4

In Vivo Established Tumor Experiments:

Five to six week old, female SCID mice were implanted with 5 million MDA-MB-231 breast cancer cells in one hundred microliters injected subcutaneously in the L scruff of the neck. Tumor growth was measured with calipers every week. When the majority of the cohort reached a tumor volume of 100 mm$^3$ (range 50-200 mm$^3$) at 34 days post implantation 8-10 mice were randomly assigned into each of three treatment groups. 7BD-33-11A, 1A245.6 test antibodies or 3BD-27 isotype control antibody (known not to bind MDA-MB-231 cells) were administered intrapertioneally with 15 mg/kg of antibodies at a volume of 150 microliters after dilution from the stock concentration with a diluent that contained 2.7 mM KCl, 1 mM KH$_2$PO$_4$, 137 mM NaCl, 20 mM Na$_2$HPO$_4$. The antibodies were then administered three times per week for 10 doses in total in the same fashion until day 56 post-implantation. Tumor growth was measured about every seventh day with calipers until day 59 post-implantation or until individual animals reached the Canadian Council for Animal Care (CCAC) end-points. Body weights of the animals were recorded for the duration of the study. At the end of the study all animals were euthanised according to CCAC guidelines.

Figure 4:
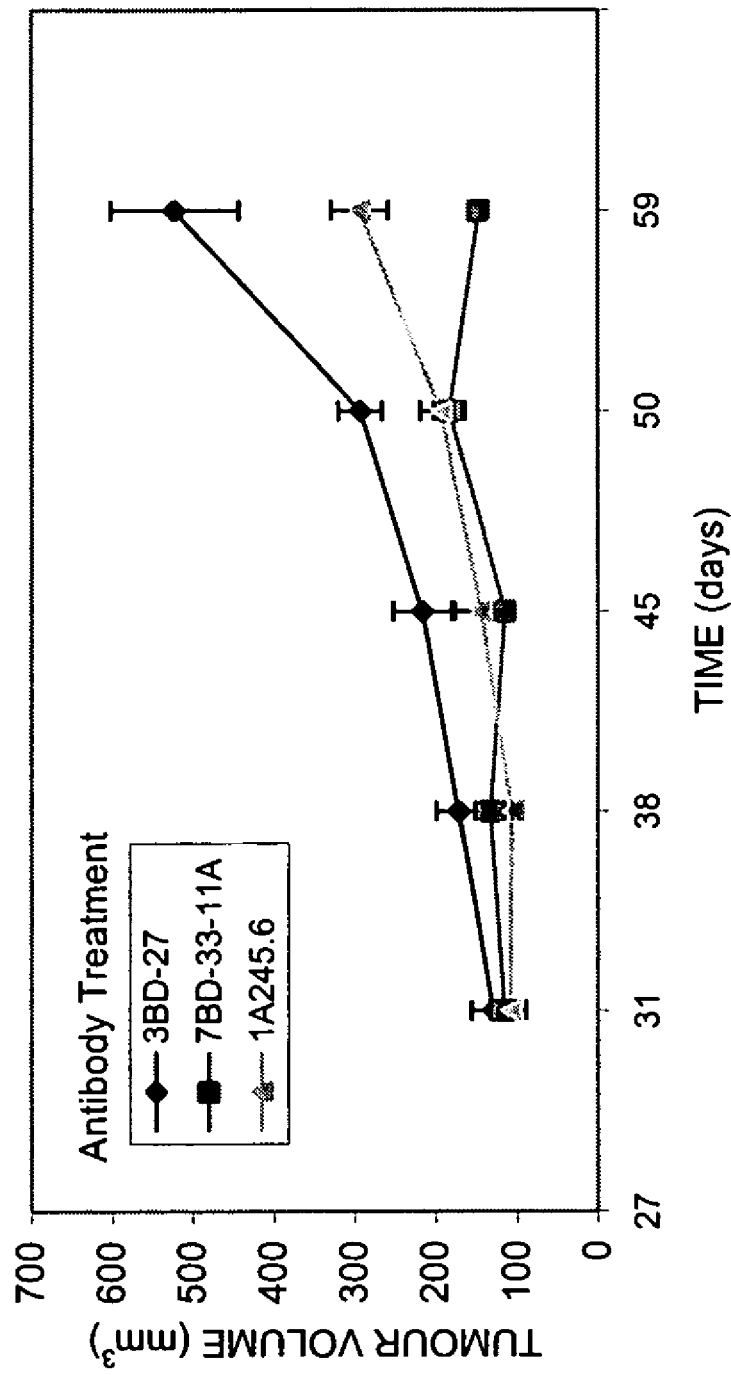
FIG. 4 is a graphical analysis of tumor volume over time with respect to particular antibody treatment.

There were no clinical signs of toxicity throughout the study. Body weight was measured at weekly intervals. There was no significant difference in weight for the groups treated with the isotype control and 7BD-33-11A, or 1A245.6 antibodies. As can be seen in FIG. 4, at day 59 post-implantation (2 days after the cessation of treatment), tumor volume of the group treated with 7BD-33-11A was 29.5% of the control group (p=0.0003). In this group, there was also a trend toward regression in mean tumor volume when the value for day 59 was compared to day 52 (p=0.25). Likewise, treatment with 1A245.6 antibody also significantly suppressed tumor growth and decreased tumor burdens. Animals with established tumors treated with this antibody had tumor volumes that were 56.3% of the isotype treated control group (p=0.017).

In toto, treatment with 7BD-33-11A or 1A245.6 antibodies significantly decreased the tumor burden of established tumors in comparison to a control antibody in a well recognized model of human cancer disease suggesting pharmacologic and pharmaceutical benefits of these antibodies for therapy in other mammals, including man.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of treating human breast and prostate tumors in a mammal, wherein said human breast and prostate tumors express an antigen which specifically binds to the isolated monoclonal antibody produced by the hybridoma deposited with the ATCC as accession number PTA-4889, a humanized version thereof, a chimeric version thereof, or antigen binding fragments thereof, comprising administering to said mammal said monoclonal antibody, said humanized version thereof, said chimeric version thereof, or antigen binding fragments thereof in an amount effective to reduce said mammal's tumor burden.

2. The method of claim 1 wherein said monoclonal antibody or antigen binding fragment thereof is conjugated to a cytotoxic moiety.

3. The method of claim 2 wherein said cytoroxic moiety is a radioactive isotope.

4. The method of claim 1 wherein said monoclonal antibody activates complement.

5. The method of claim 1 wherein said monoclonal antibody mediates antibody dependent cellular cytotoxicity.

* * * * *